United States Patent [19]
Hall et al.

[11] Patent Number: 5,460,595
[45] Date of Patent: Oct. 24, 1995

[54] MULTI-FREQUENCY ULTRASOUND THERAPY SYSTEMS AND METHODS

[75] Inventors: Duane O. Hall, Sandy, Utah; Alan R. Selfridge, Los Gatos, Calif.

[73] Assignee: Dynatronics Laser Corporation, Salt Lake City, Utah

[21] Appl. No.: 70,533

[22] Filed: Jun. 1, 1993

[51] Int. Cl.$^6$ ............................................. A61H 1/00
[52] U.S. Cl. ........................... 601/2; 604/22; 310/316; 310/317; 310/320; 73/579
[58] Field of Search ................... 601/2; 128/660.01; 607/97; 310/314–320; 604/22; 73/579

[56] References Cited

U.S. PATENT DOCUMENTS

| | | | |
|---|---|---|---|
| Re. 33,672 | 8/1991 | Miwa | 128/660 |
| 4,368,410 | 1/1983 | Hance et al. | 318/116 |
| 4,535,777 | 8/1985 | Castel | 128/421 |
| 4,564,019 | 1/1986 | Miwa | 128/660 |
| 4,747,820 | 5/1988 | Hornlein et al. | 604/22 |
| 4,768,496 | 9/1988 | Kreizman et al. | 601/2 |
| 4,966,131 | 10/1990 | Houghton et al. | 601/2 |
| 5,151,085 | 9/1992 | Sakurai et al. | 604/22 |
| 5,184,605 | 2/1993 | Grzesykowski | 601/2 |

OTHER PUBLICATIONS

Emmanuel Papadakis, *The Journal of Adhesion*, "Nonuniform Pressure Device for Bonding Thin Slabs to Substrates", vol. 3, pp. 181–194, 1971 (U.S.A.).

Primary Examiner—Krista M. Zele
Attorney, Agent, or Firm—Berne S. Broadbent; Gary D. E. Pierce

[57] ABSTRACT

An ultrasound therapy system and method for providing therapeutic treatment to tissues using multiple, user-selectable frequencies generated from a single applicator sound head. The multi-frequency ultrasound therapy system and method includes a generator/control unit having a microprocessor for controlling and monitoring the generation and output of ultrasonic energy. A precision oscillator is connected to the microprocessor, and wave shaping circuitry is also provided to generate a wave-form for amplification by an output amplifier. The amplified high frequency waveform is supplied to and drives an applicator sound head at an appropriate frequency for producing the desired therapeutic ultrasonic waves for treatment. Bonded to a cup member and positioned within the applicator sound head is a transducer crystal which converts high frequency wave-forms into mechanical (acoustic) vibrations, thus producing thermal energy in the form of heat for penetration into tissues under treatment. Both the transducer crystal and the applicator cup are designed with the capability of providing at least three different output frequencies from a single applicator sound head, while supplying three different penetration depths for treating a patient's tissues.

20 Claims, 12 Drawing Sheets

MULTI-FREQUENCY ULTRASOUND THERAPY SYSTEMS AND METHODS

BACKGROUND

1. The Field of the Invention

This invention relates to ultrasound therapy devices and, more particularly, to novel systems and methods for providing ultrasound therapy at multiple, user-selectable frequencies using a single applicator sound head.

2. The Background Art

Heat has long been known to have many beneficial and necessary effects in the rehabilitation process. Heat increases the extensibility of collagen tissue, decreases joint stiffness, produces pain relief, relieves muscle spasm, increases blood flow, increases local metabolism, increases nerve conduction velocities, and assists in the resolution of inflammatory infiltrates, edema, and exudates. Heat has also been used as part of cancer therapy.

Investigations have shown that subjective complaints of stiffness on the part of a patient with rheumatoid arthritis coincide with changes in the measurements of the viscoelastic properties of joints. The joint stiffness, assessed both subjectively and by objective measurement, can be decreased by the application of heat, thereby decreasing the patient's discomfort.

After hot packs, ultrasound is probably the most frequently used physical agent in treating musculoskeletal pain and soft tissue injuries. Millions of ultrasound treatments are performed each year in the United States and Canada. Ultrasound produces the desirable therapeutic effects of any deep-heat modality. The effect of ultrasound that may be the most distinguishable, however, is its ability to selectively increase the temperature in local, well-circumscribed areas.

Ultrasound is a form of acoustic vibration occurring at frequencies too high to be perceived by the human ear. Thus, frequencies under 17,000 Hz are usually called sound, whereas those above this level are designated ultrasound. With the exception of the differences in frequencies, the physics of ultrasound is in no way different from that of audible sound. Ultrasonic frequencies typically used for therapeutic purposes range between 0.8 and 3 MHz.

The temperature distribution produced by ultrasound is unique among deep-heating modalities. Ultrasound causes comparatively little temperature elevation in the superficial tissues, but has a depth of penetration in the musculature and other soft tissues. In normal biological applications, for example, about 50% of the ultrasound energy is transmitted to a depth of 5 cm (1 inch) or greater, and this depth of penetration can be effectively employed in reaching deep tissues, such as joint capsules and deep muscles. For this reason, ultrasound is generally the treatment of choice when it is desirable to provide deep heat.

The therapeutic ultrasound machine consists of a generator that produces a high-frequency alternating current. The high frequency electric current is then converted by a transducer into mechanical (acoustic) vibrations. The transducer consists basically of a crystal inserted between two electrodes. As an alternating electrical charge is applied to the surfaces of the crystal, the crystal is made to vibrate. As the crystal vibrates rapidly, sound waves are produced.

Ultrasound waves are transmitted more effectively through water, oil, or transmission gel than air. Consequently, a coupling agent is used in clinical applications to "couple" the applicator sound head to the patient's body in order to ensure that the ultrasonic waves are properly transmitted to the desired treatment site. Such a coupling agent may, for example, be in the form of a gel or lotion which is applied to the skin of the patient over the area to be treated. Water may also be used as a coupling agent in appropriate cases by submerging a portion of the patient's body in a water bath. The sound head is then positioned in the coupling agent over the patient's skin, and the generator is activated. Ultrasonic waves produced at the sound head are transmitted through the coupling agent into the patient to provide the desired therapeutic treatment.

The treatment properties of the sound applicator depend upon its diameter and frequency. For example, a small diameter applicator produces a small diameter ultrasound beam. The angle of divergence of the beam is also generally greater than if a larger diameter applicator is used. For this reason, it may be difficult to treat the deep tissues in an area using a small diameter applicator. On the other hand, if the radiating surface of the applicator is too large, it may be difficult to maintain contact with the surface of the body at all times. Consequently, applicators of different sizes are generally provided with ultrasound equipment, and the size used will depend upon the nature of the treatment being performed.

Similarly, ultrasound frequencies of about 1 MHz are typically used to treat deep tissue, while higher frequencies do not penetrate the patient as deeply. A practitioner will thus decide which frequency to use depending upon the patient's condition. Unfortunately, however, prior art ultrasound devices typically have sound heads which are capable of operating effectively at only a single frequency. Consequently, the user will generally be required to purchase several different sound heads of each size in order to provide the varying penetration depths needed for different therapeutic treatments.

The need to use several different sound heads in order to provide ultrasonic therapy is, of course, a significant expense. For example, if a user wishes to have three different frequencies available on three different sizes of sound head, nine separate sound heads would have to be supplied.

Moreover, the sound heads would need to be changed in order to vary the ultrasound frequency, as well as to vary the head size. Changing sound heads can be both time-consuming and cumbersome since the operational parameters of the ultrasound equipment must be readjusted each time the head is changed.

BRIEF SUMMARY AND OBJECTS OF THE INVENTION

In view of the foregoing, it is a primary object of the present invention to provide an ultrasound therapy system and method having a single sound applicator head which is capable of operating at three different frequencies, thereby eliminating the need to have a separate head for each frequency.

It is also an object of the present invention to provide an ultrasound therapy system and method which uses a microprocessor to detect the size of applicator head being used and to thereafter control and monitor all functional aspects of the generation and output of ultrasound waves.

Further, it is an object of the present invention to provide an ultrasound therapy system and method which simplifies use and decreases manufacturing costs.

Consistent with the foregoing objects, and in accordance with the invention as embodied and broadly described herein, an ultrasound therapy system is disclosed in one embodiment of the present invention as including a generator/control unit having a microprocessor for controlling and monitoring the generation and output of ultrasonic energy. Connected to the microprocessor is a precision oscillator providing wave shaping circuitry to generate a wave-form which is further amplified by an output amplifier.

The amplified high frequency wave-form is supplied to and drives an applicator sound head at the appropriate output frequency, whereby producing the desired ultrasonic waves for therapeutic treatment. Positioned within the applicator sound head is a transducer crystal which converts high frequency electrical signals into mechanical (acoustic) vibrations, thus producing thermal energy in the form of heat for deep penetration into those tissues being treated. Both the transducer crystal and the applicator cup are designed with the capability of providing at least three different output frequencies from a single applicator sound head, while supplying three different penetration depths for treating a patient's tissues.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 4, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

Figure 1:
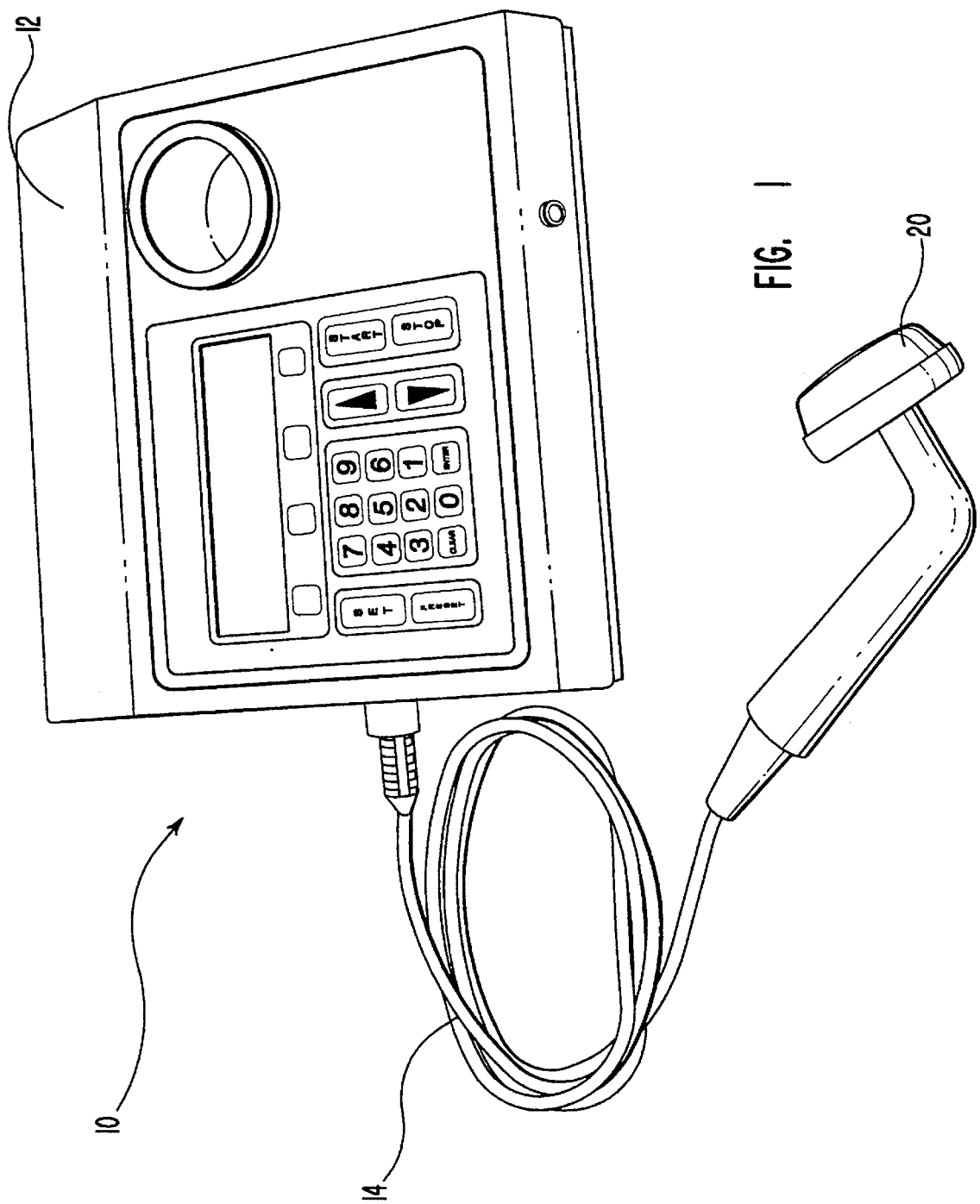
FIG. 1 is a perspective view of a multi-frequency ultrasound therapy system in accordance with one presently preferred embodiment of the present invention.

One presently preferred embodiment of the multi-frequency ultrasound therapy system of the present invention, designated generally at 10, is illustrated in FIG. 1. As shown, ultrasound system 10 comprises an ultrasound generator/control unit 12 and an applicator sound head 20. Applicator head 20 is removably connected to generator/control unit 12 by means of an electrical cord 14.

Figure 2:
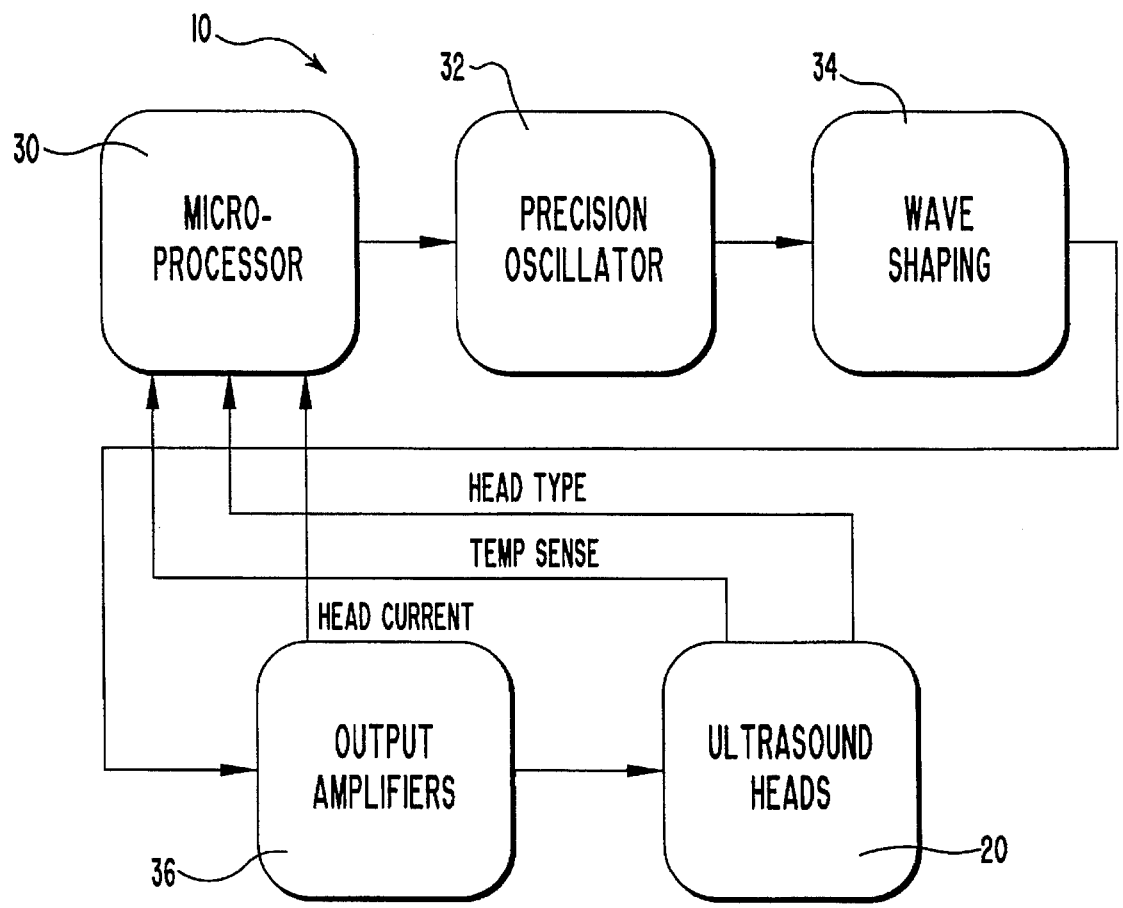
FIG. 2 is a functional block diagram illustrating one presently preferred embodiment of the multi-frequency ultrasound therapy system and method of the present invention.

Referring now to the functional block diagram of FIG. 2, ultrasound system 10 includes a microprocessor 30 which controls and monitors the ultrasound generation and output. Microprocessor 30 is connected to and controls a precision oscillator 32. The output of precision oscillator 32 is provided to wave shaping circuitry 34, and the generated wave-form is amplified by means of output amplifiers 36. The amplified wave-form is supplied to and drives the ultrasound applicator head 20 at the appropriate frequency, thereby producing the desired ultrasonic waves for use in treatment.

The central component of applicator head 20 is a transducer crystal for converting electrical signals into ultrasonic waves. This transducer crystal is provided with electrodes in conventional fashion and is electrically connected to generator/control unit 12 via cable 14 (see FIG. 1). Apart from the novel transducer configuration described below, the overall structure of applicator head 20 is substantially the same as that of other applicator heads used for ultrasound therapy and is believed to be well known in the art to which this invention pertains. The overall structure and configuration of applicator head 20 will not, therefore, be described in further detail herein.

Figure 3:
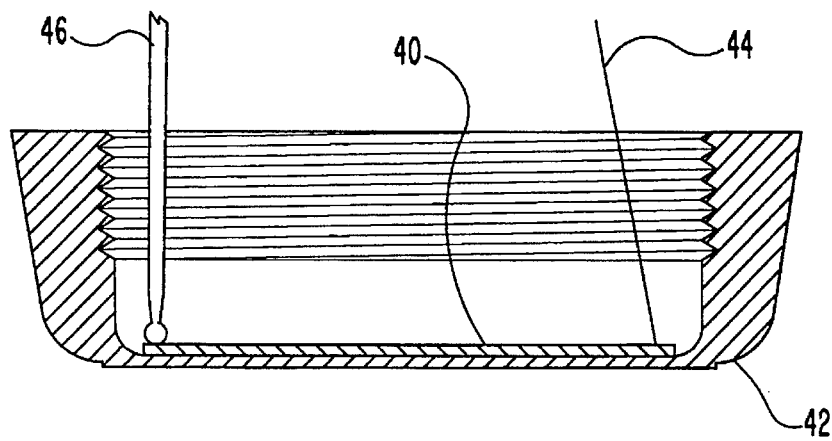
FIG. 3 is a cross-sectional view of one presently preferred embodiment of the transducer and cup of one presently preferred embodiment of the applicator head of the ultrasound therapy system of the present invention.
Figure 4A:
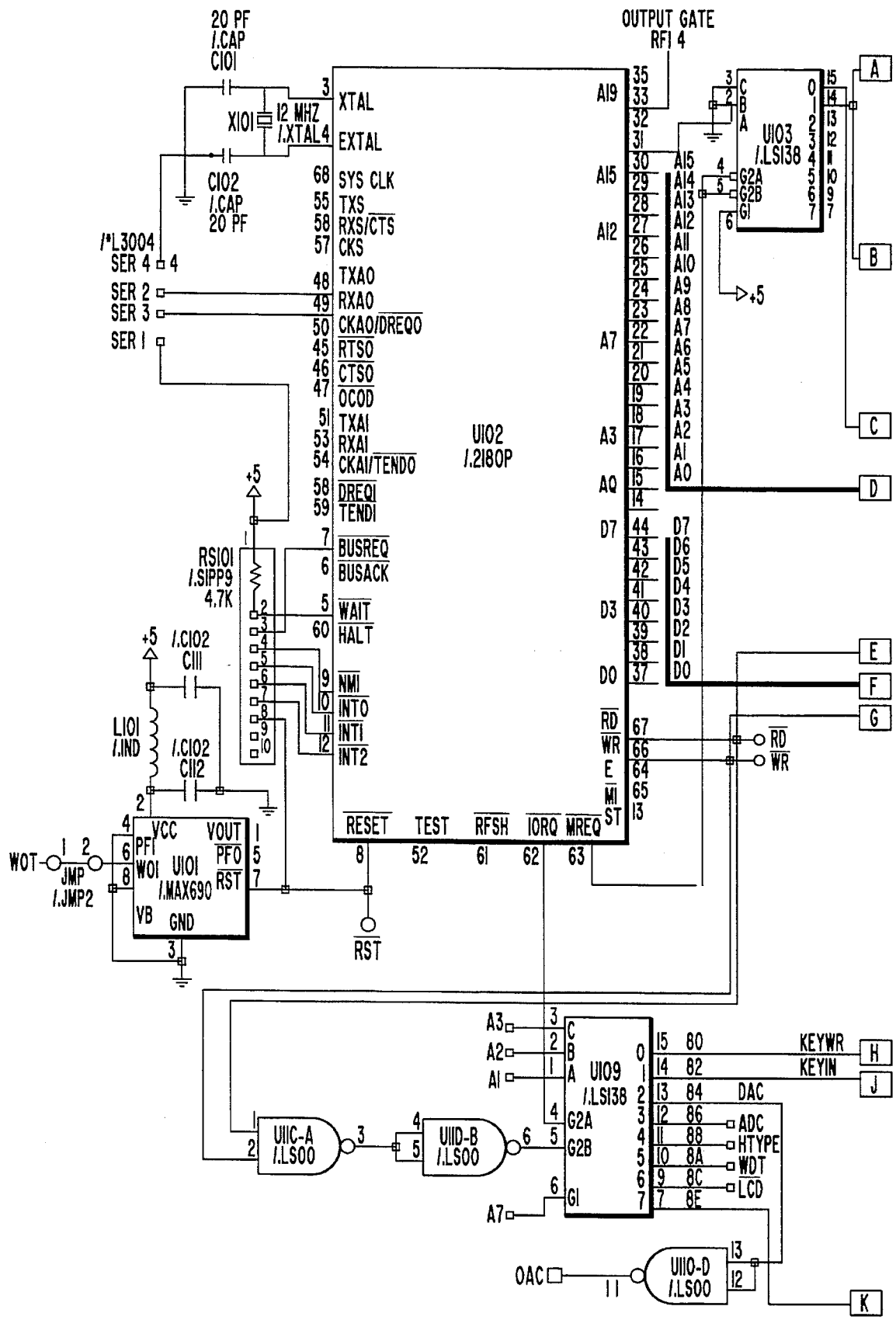
FIGS. 4A through 4E (hereinafter referred to collectively as FIG. 4), are an electrical schematic diagram illustrating one presently preferred configuration of an electrical circuit for use in connection with one presently preferred embodiment of the multi-frequency ultrasound therapy system and method of the present invention. (It should be noted that FIGS. 4A through 4E comprise a single schematic diagram, the labeled tabs illustrating the electrical interconnection between the Figures.)
Figure 4B:
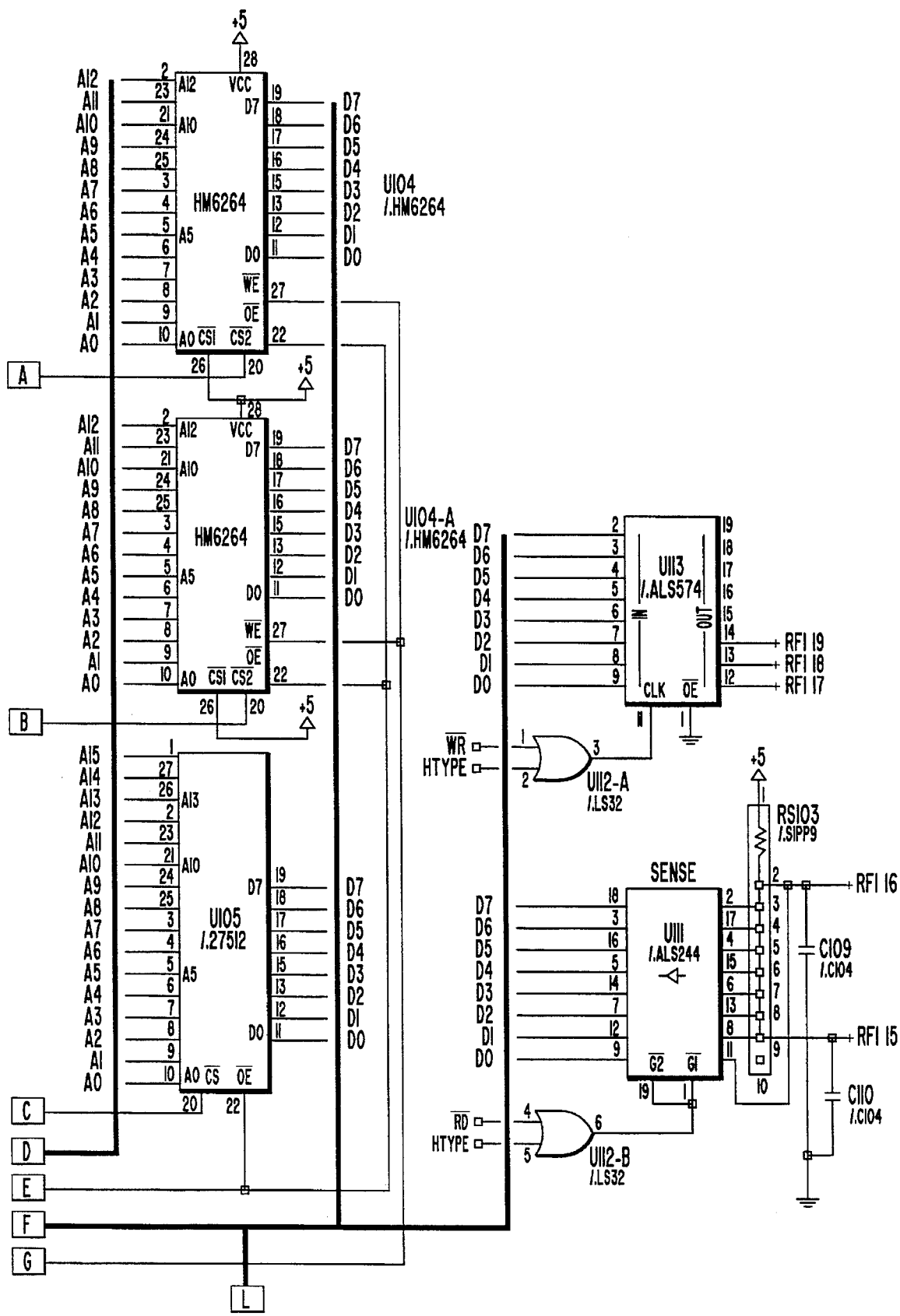
Figure 4C:
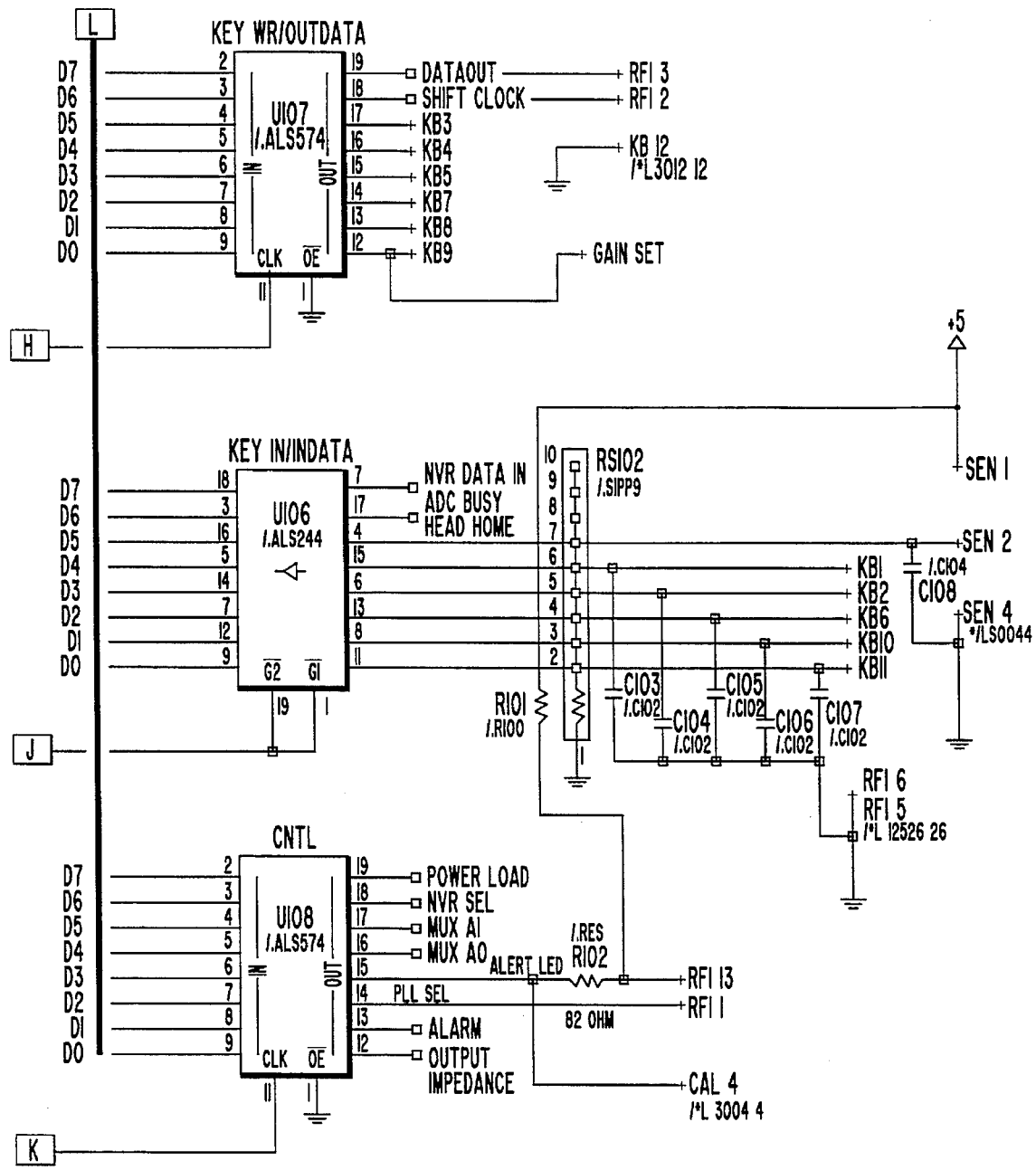
Figure 4D:
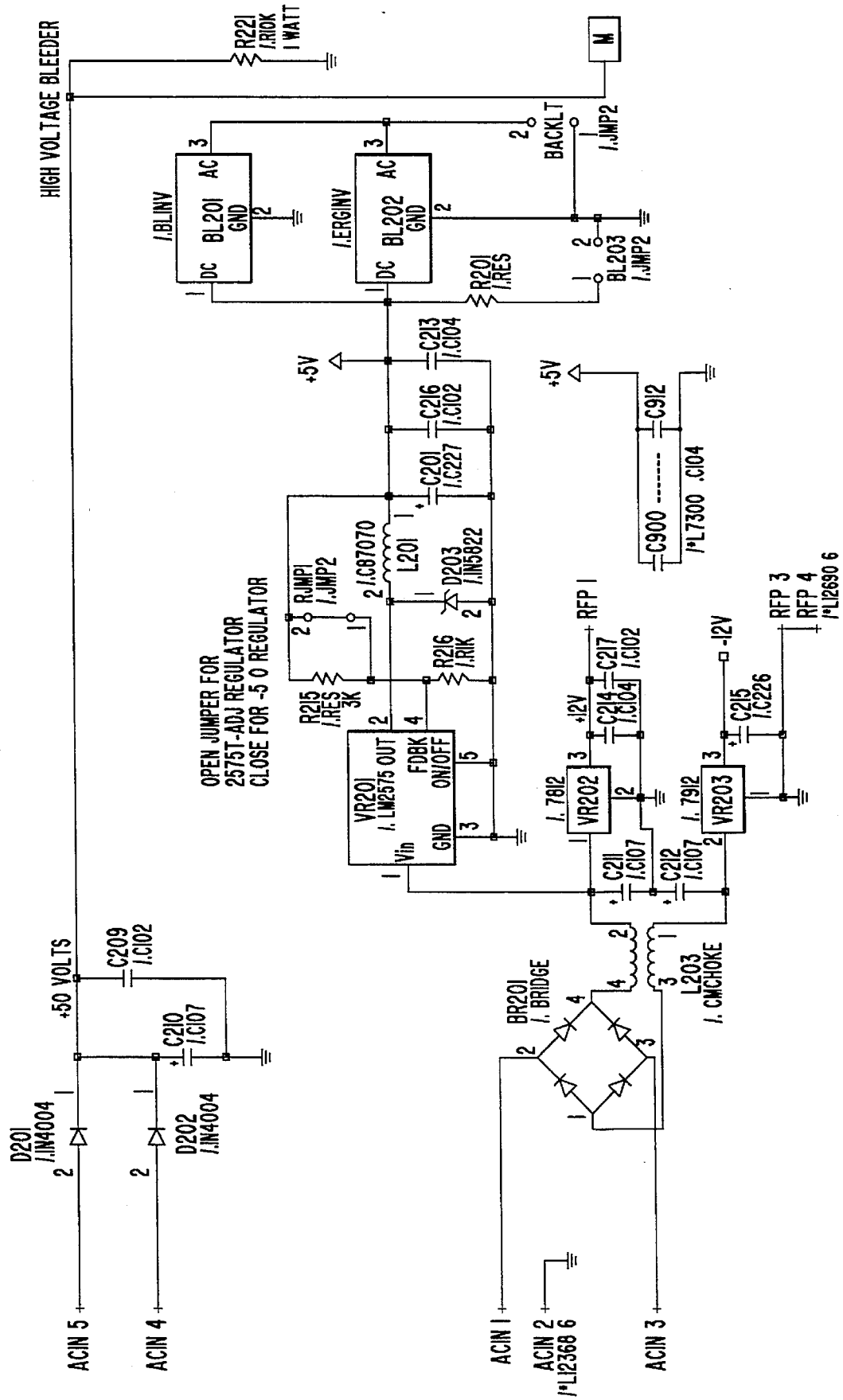
Figure 4E:
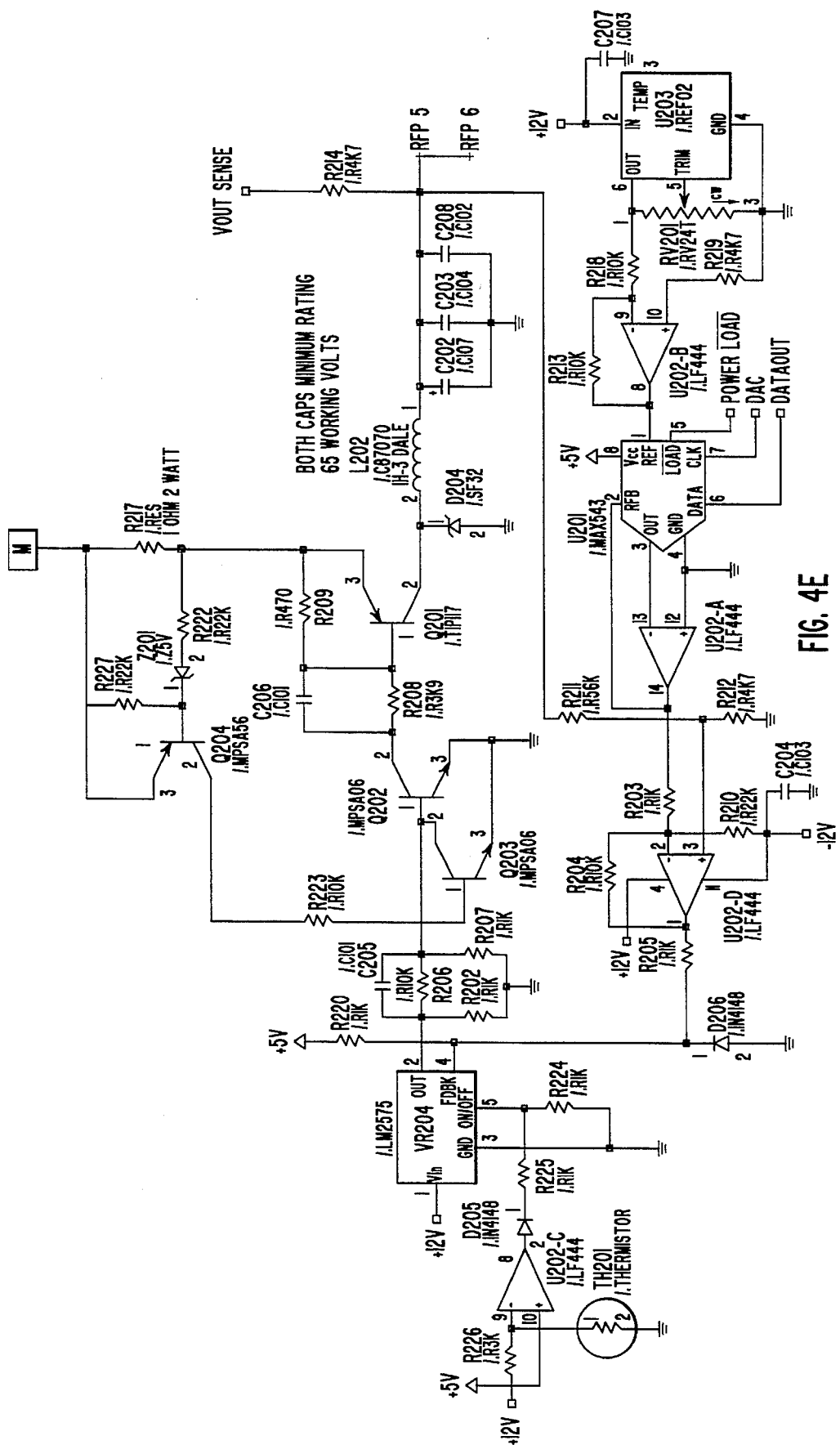
Figure 4F:
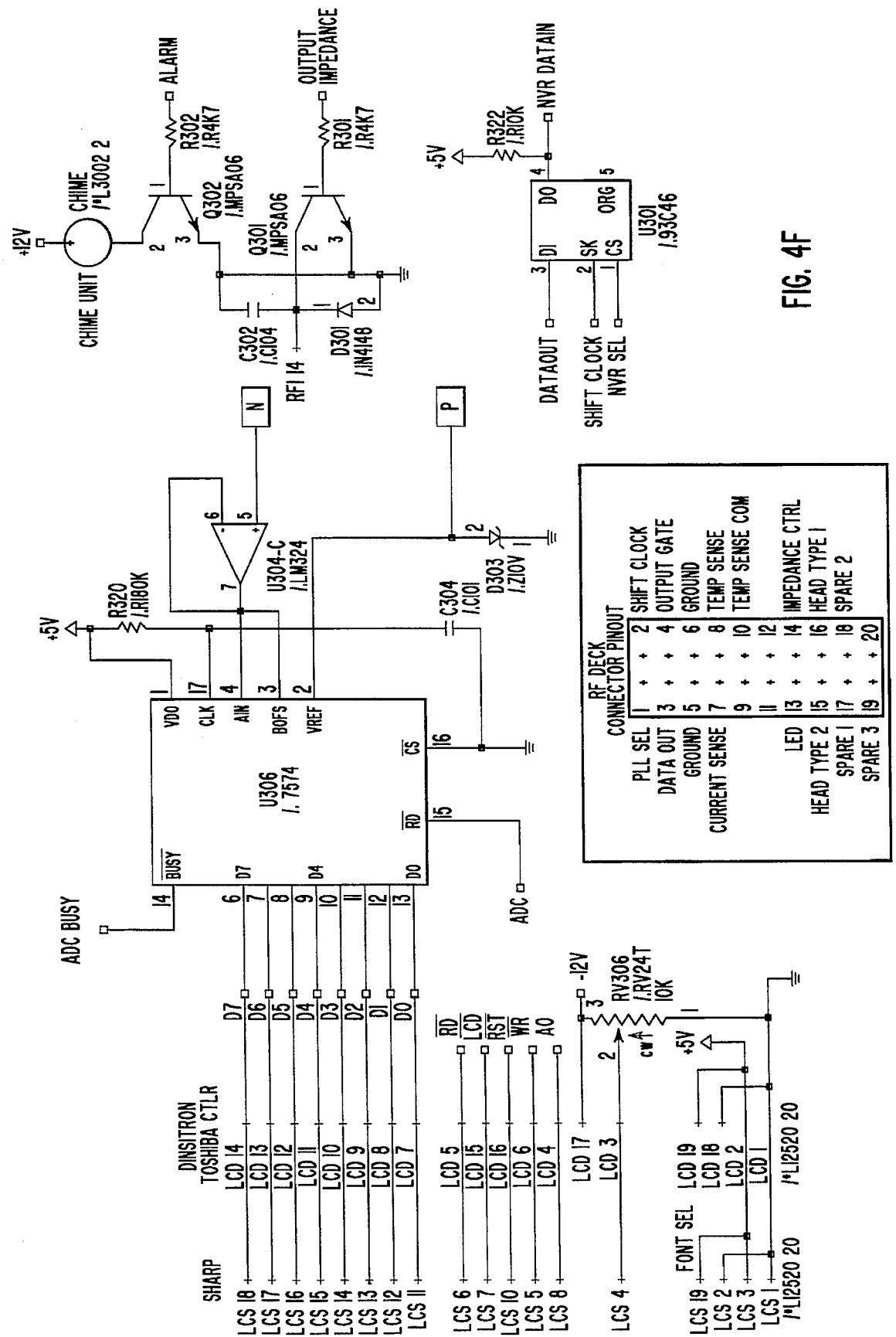
Figure 4G:
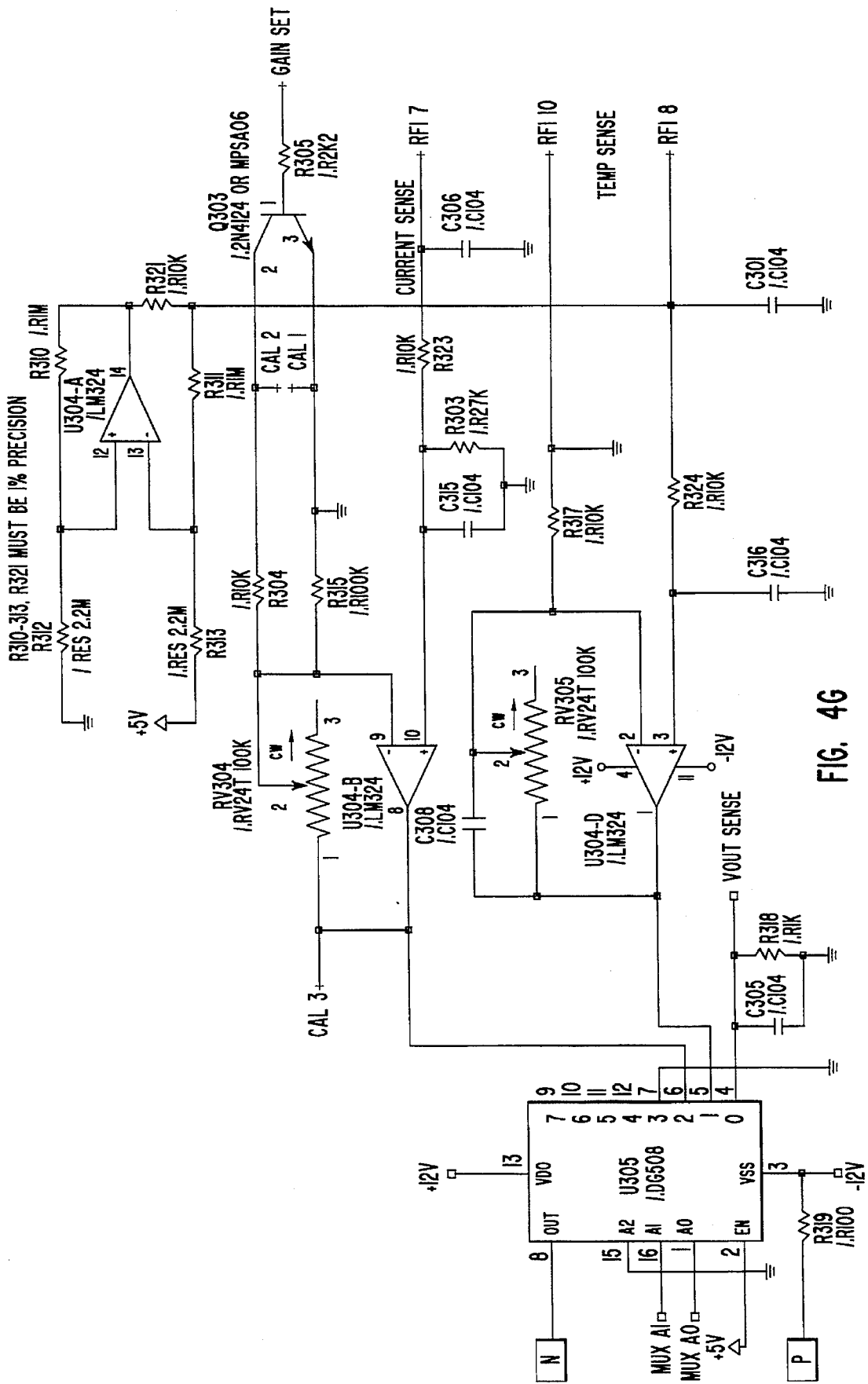
Figure 4H:
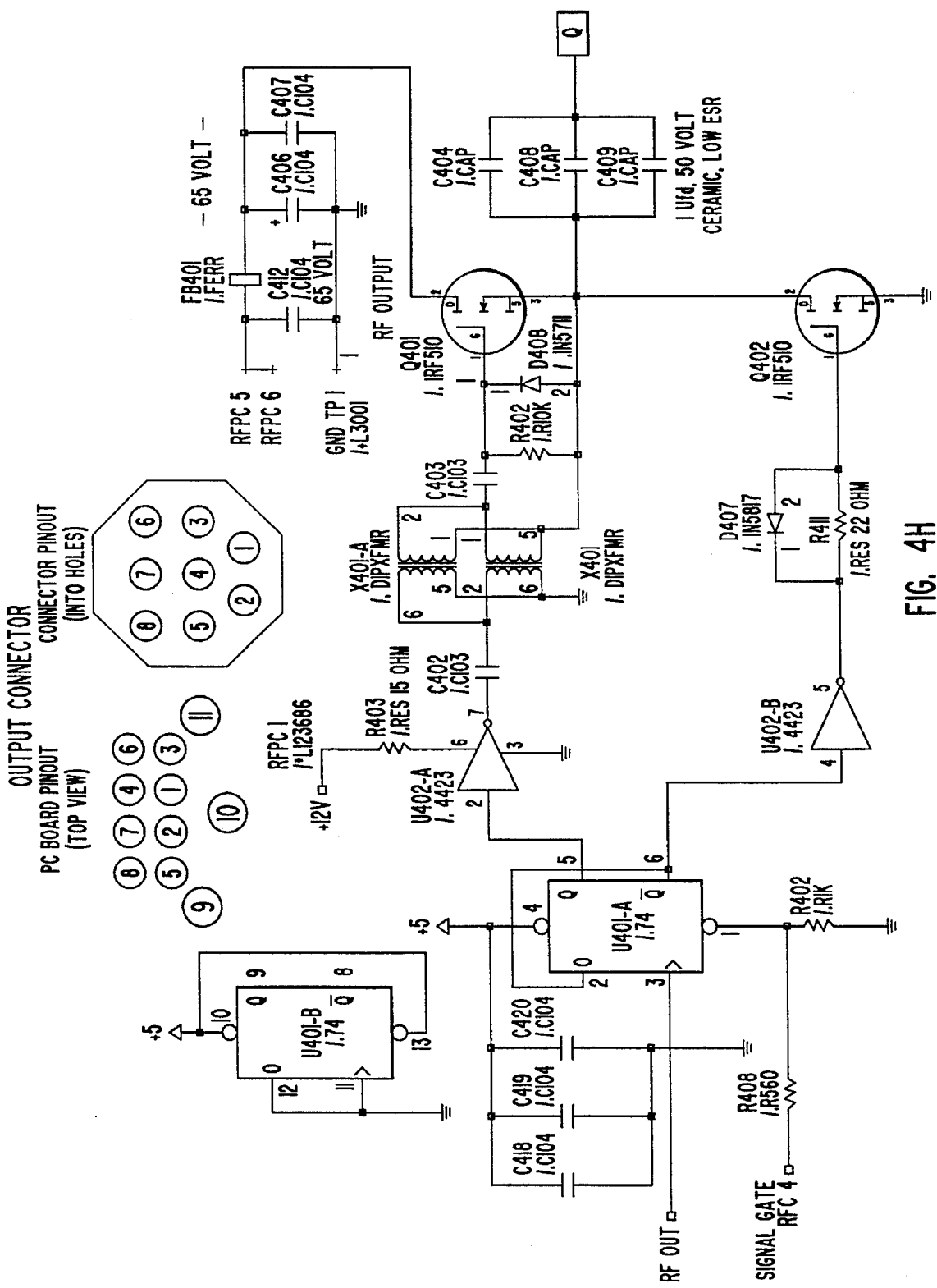
Figure 4I:
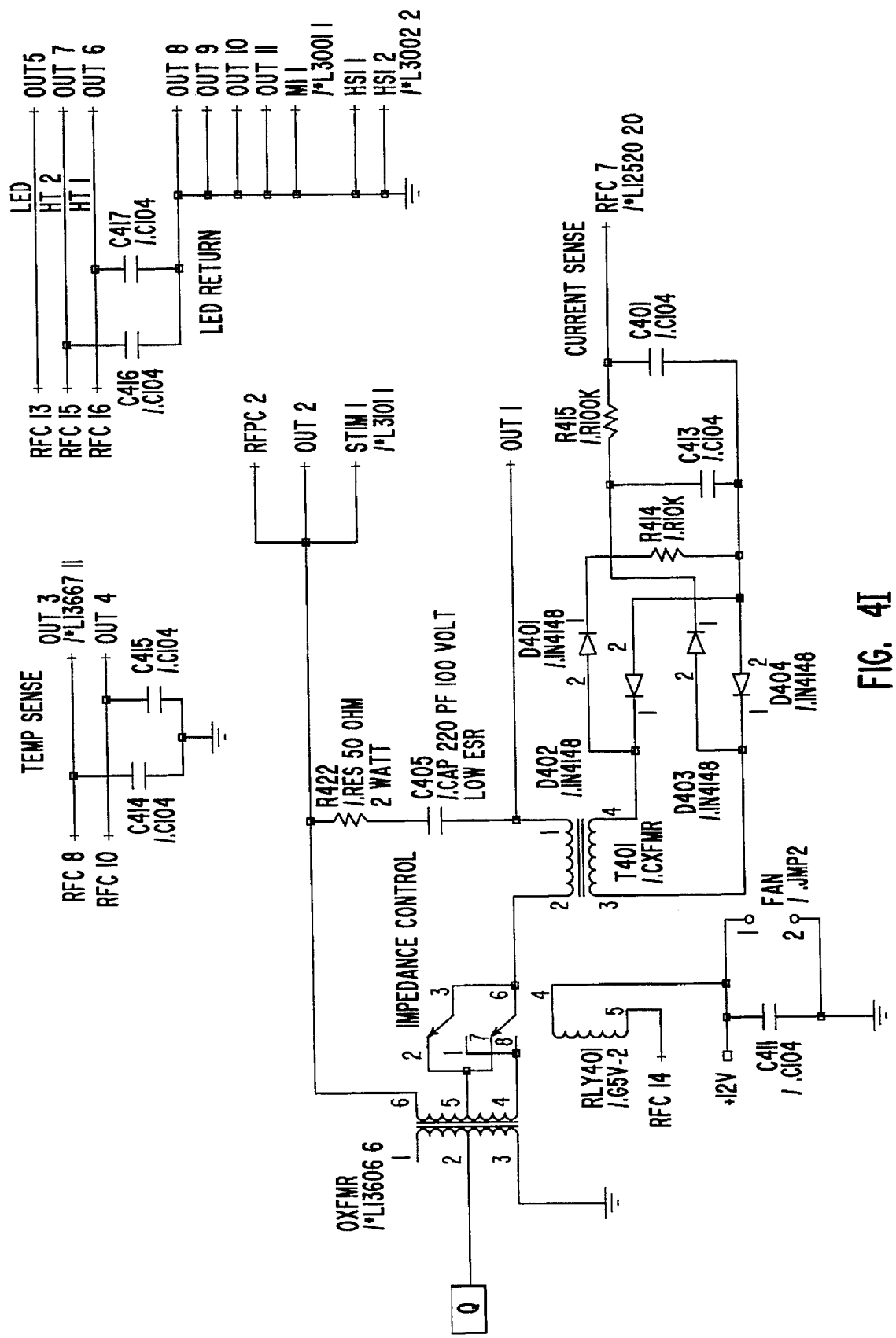
Figure 4J:
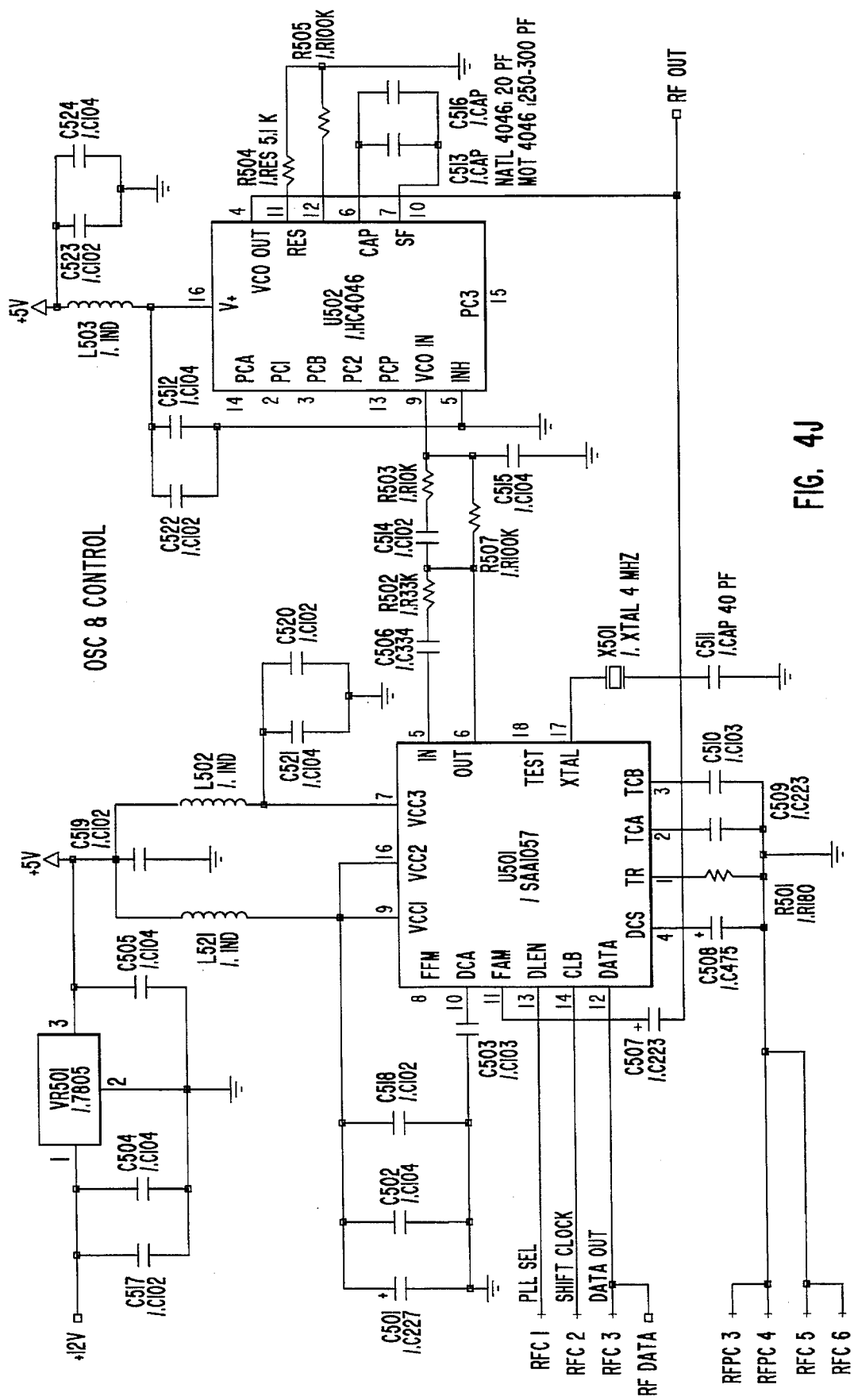

As depicted in cross-section in FIG. 3, the transducer crystal of applicator head 20 comprises a ceramic crystal 40 which is bonded to an aluminum alloy applicator cup 42. Significantly, crystal 40 and cup 42 are capable of producing three different frequencies of ultrasonic waves. In one presently preferred embodiment, for example, crystal 40 and cup 42 positioned within the applicator head 20 can produce nominal frequencies of 1 Mhz, 2 Mhz and 3 Mhz. Advantageously, therefore, a single applicator head 20 can be used to provide ultrasound therapy at three different frequencies, and, as a result, at three different tissue depths within a patient.

Crystal 40 is formed of a suitable poled ceramic material, such as, for example, a high Q ceramic material such as EC97 from EDO Western Corp. The ceramic is formed and prepared in a manner well known in the art to have a natural resonance at 2 Mhz (that is, the ceramic is formed so as to be one-half wavelength thick at 2 Mhz). Thus, for example, the ceramic may be 0.0431 inch (1.0947 mm) thick.

Applicator cup 42, on the other hand, is formed of an aluminum alloy. This alloy is preferably hard enough to resist excessive abrasion during use and may, for example, be alloy 6262T8. Applicator cup 42 is likewise formed and prepared to have a natural resonant frequency of 2 Mhz.

In order to achieve multiple resonances reliably, both crystal 40 and cup 42 are fabricated to thickness and flatness tolerances of 0.0005 inch (0.01270 mm). In addition, the thickness of the glue bond between crystal 40 and cup 42 is maintained at very nearly zero.

The thin bonding of crystal 40 to applicator cup 42 can be done reliably by the following procedure to yield epoxy bonds on the order of 1 to 2 μm thick. The bonds will have excellent adhesion, and it is not necessary to heat the parts being bonded. Room temperature bonding is especially important when the pieces being bonded have different coefficients of thermal expansion, as do ceramic and aluminum. When such pieces are bonded together at elevated temperatures, they may crack or distort when they cool down.

The ceramic slab and the aluminum cup are first cleaned and then bonded to each other using a very thin (low viscosity) epoxy adhesive. For example, Dow epoxy resin (DER) 332 may be melted in a disposable beaker of known weight. After the resin is in a liquid state at room temperature, 11 PHR of Dow epoxy hardener (DEH) 20 is added using an eye dropper. Both DER 332 and DEH 20 are manufactured by Dow Chemical Company and are available from a number of commercial vendors. One should exercise caution when using these substances, since DEH 20 is a diethyl triamine and is therefore volatile and fumes when opened; and it is also an irritant with a SPI classification 5. Even the epoxy will fume as it cures. Despite these hazards, however, this adhesive has been found to give very excellent results at room temperature. DEH 20 yields bonds with excellent adhesion and also seems to lower the viscosity of the resin significantly, which is another desirable property for making thin bonds.

It is convenient to use a hypodermic needle to deliver the epoxy to the pieces being bonded. Thus, for example, after mixing the hardener with the resin, one or two ml of the epoxy can be poured into a 10 cc Luer-LOK disposable syringe (B-D #5604 from Becton, Dickinson, and Co., Rutherford, N.J.). Next a disposable micropore filter is attached to the syringe, along with a 23 gauge, 1 inch (2.54 cm) needle. The first few drops delivered by the needle are preferably discarded to help insure that the epoxy used in making the bond is not contaminated. A bead of filtered epoxy is placed over the center of one of the parts being bonded, and the other piece is laid down on top of the glue using clean tweezers. Air bubbles in the glue bead must be dealt with either by pushing them off one end of the glue bead, popping them, or by sucking them up with the syringe.

The next step in thin bonding is to press out almost all of the epoxy between the pieces being bonded. To do this we employ the nonuniform pressure bonding technique of E. P. Papadakis (*Journal of Adhesion*, "Nonuniform Pressure Device for Bonding Thin Slabs to Substrates," 1971, Vol. 3, pp. 181–94). The idea behind this technique is to apply more pressure to the center of the parts being bonded than one applies to the edges, thereby avoiding the problem of having epoxy trapped between. This is accomplished by using a jig and a spherical piece of rubber to press the ceramic slab against the aluminum, thereby exerting more force at the center of the ceramic than we do at the edges. After two days, the bonded parts are removed from the bonding jig. Excess epoxy can be removed with an epoxy stripper or Miller Stevenson Product #MS111.

As mentioned above, crystal 40 is provided with electrodes (not shown) in a manner which is well known in the art (such as by vapor deposition). An electrical lead 44 is soldered to the electrode of crystal 40 to provide the needed electrical connection. A thermistor 46 is also provided in order to sense the temperature of crystal 40, for reasons which will become readily apparent from the discussion which follows.

The combination of ceramic and aluminum layers, as described above, results in a crystal having a natural resonance at 2 MHz, with additional, useable resonances at 1 and 3 MHz. In addition, the use of Aluminum in combination with the ceramic provides a transition between the acoustic impedance of the ceramic and that of the human body. It has also been observed that the transducer bandwidth is increased, and stressing of the ceramic is reduced.

Referring again to FIG. 2, when ultrasound system 10 is first activated, applicator head 20 is scanned at a first known temperature through each of the three output frequency levels to determine the specific driving frequency of maximum efficiency at each level. The scanning of applicator head 20 is then repeated at a second, higher temperature. Finally, a known output (as measured by an ultrasonic power meter) is generated, and the impedance of applicator head 20 is calculated from the detected output voltage and current. For each of the three output frequencies, microprocessor 30 then stores the following three parameters for later use: (1) frequency of output, (2) head impedance, and (3) frequency change over the operating temperature.

During operation, the temperature and output current for each of the three output frequencies of applicator head 20 is continuously monitored by microprocessor 30. The driving frequency generated by oscillator 32 is adjusted, as needed, to maintain optimum ultrasonic output over the operating temperature range. If the temperature of applicator head 20 exceeds a pre-set safe level, microprocessor 30 actuates a warning signal (such as a bell and/or display screen), and operation is disabled until the temperature of applicator head 30 returns to a safe level. Applicator head 30 is thus protected from damage in situations where poor coupling results in self-heating.

Reference is next made to FIG. 4, which illustrates in more detail one preferred embodiment of a schematic diagram derived from the functional block diagram of FIG. 2. Those of ordinary skill in the art will, of course, appreciate that various modifications to the detailed schematic diagram of FIG. 4 may easily be made without departing from the essential characteristics of the invention, as described in connection with the block diagram of FIG. 2 above. Thus, the detailed schematic diagram of FIG. 4 is intended only as an example, and it simply illustrates one presently preferred embodiment of a schematic diagram that is consistent with the foregoing description of FIG. 2 and the invention as claimed herein.

In FIG. 4, the designations "RFI" and "RFC" refer to electrical contacts at opposite ends of a ribbon cable which interconnects portions of the circuitry. RFI 1 thus connects to RFC 1, and so forth. Similarly, the designations "RFP" and "RFPC" refer to electrical contacts at opposite ends of a power cable, with RFP 1 connecting to RFPC 1, etc.

Table 1 below identifies the specific electrical components illustrated in FIG. 4. Unless other wise noted, capacitors have 0.2 inch (5.08 mm) spacing and are 25 volt, and resistors are 0.25 watt.

TABLE 1

| No. | Description | Manufacturer | Part Number |
| --- | --- | --- | --- |
| C101, 102 | Cap 20 pf 25 Volt Ceramic | | |

TABLE 1-continued

| No. | Description | Manufacturer | Part Number |
|---|---|---|---|
| C205, 304 | Cap 100 pf 25 Volt Ceramic | | |
| C103–107 | Cap .001 µf 25 Volt Ceramic | | |
| C108, 109, 110, 213, 214, 301, 302, 305, 306, 308, 315, 316 | Cap .1 µf 50 Volt Ceramic | | |
| C900–912 | Cap .1 Ufd 50 Ceramic, 0.3" lead spacing | | |
| C203 | Cap .1 Ufd 100 Volt Ceramic | | |
| C215 | Cap 22 µf 16 Volt Tant. Radial | | |
| C202 | Cap 100 µf 63 Volt Elec. Radial | | |
| C201 | Cap 470 µf 15 Volt Elec. Radial | | |
| C210 | Cap 1000 µf 100 volt al. elec. axial | | |
| C211, 212 | Cap 1000 µf 50 volt al. elec. axial | | |
| C511, 513 | 39 pf | | |
| C405 | 200 Pf 100 Volt low ESR | | |
| C516 | 200 pf | | |
| C509, 507 | .022 Ceramic | | |
| C402, 403, 503, 510, 601 | .01 Ufd Ceramic | | |
| C401, 411, 413, 414, 415, 416, 417, 418, 419, 420, 502, 504, 505, 512, 515 | 0.1 Ufd Ceramic | | |
| C406, 410, 412 | .1 Ufd, 65–100 volt Ceramic | | |
| C506, 514 | .33 Ufd Mono cer | | |
| C404, 408, 409 | 1 Ufd 50 Volt Ceramic, low ESR | Kemet | C330C105K5R5CA C340C105M105CA |
| C508 | 4.7 Ufd Tank, 10 volts | | |
| C407 | 100 Ufd 63 Volt Al Elect | | |
| C501 | 220 Ufd Tant 10 Volts or higher | | |
| R217 | 2 Ohm 2 Watt | | |
| R201 | 3.9 Ohm | | |
| R102 | 82 Ohm | | |
| R101, 319 | 100 Ohm | | |
| R209 | 470 Ohm | | |
| R202, 203, 205, 207, 216, 220, 318 | 1K | | |
| R305 | 2.2K | | |
| R215 | 3K | | |
| R208 | 3.9K | | |
| R212, 214, 219, 301, 302 | 4.7K | | |
| R204, 206, 213, 218, 304, 317, 322, 323, 324 | 10K | | |
| R221 | 10K 2 Watt | | |
| R210 | 22K | | |
| R303 | 27K | | |
| R211 | 56K | | |
| R315 | 100K | | |

TABLE 1-continued

| No. | Description | Manufacturer | Part Number |
|---|---|---|---|
| R320 | 180K | | |
| R310, 311 | 1 Meg 1% | | |
| R312, 313 | 2.2 Meg 1% | | |
| RS101, 102 | 4.7K Ohm Sip 9 Pin Bussed | Bourns | 10X-1-472 |
| R403 | 15 Ohm | | |
| R411 | 22 Ohm | | |
| R604 | 39 Ohm | | |
| R501 | 180 Ohm | | |
| R408 | 560 Ohm | | |
| R402 | 1K | | |
| R606 | 2.2K | | |
| R503 | 3K | | |
| R504 | 5.1K | | |
| R401, 414, 602, 603 | 10K | | |
| R502 | 33K | | |
| R415, 505, 507 | 100K | | |
| R605 | 390K | | |
| R601 | 680K | | |
| R422 | 50 Ohm 2 Watt Non-inductive | | |
| RV201 | Pot 10K 17 Turn Vert Adj. | Bourns | 3296W-1-103 |
| RV304, 305 | Pot 100K 17 Turn Vert Adj. | Bourns Spectrol | 3296W-1-104 68WR104 |
| RV306 | Pot 10K 1 Turn | Bourns | 3386T-1-103 |
| D206, 301 | Diode 1N4148 Si Gen Purpose | | 1N4148 |
| D201, 202 | Diode 1N4004 | | 1N4004 |
| D203 | Diode 1N5822 | | 1N5822 |
| BR201 | Bridge Rectifier 4 AMP 100 volt | GI | KBU4A |
| D204 | Diode SF32 Schottky 300 Volt (Diodes Inc.) | SF32 | |
| Z303 | Zener Diode 10 Volt ½ Watt | | 1N758A, 1N4740 |
| Q 2 0 2 301 (Q3), 302, 303 | Transistor MPSA06 | | MPSA06 |
| Q201 | Transistor TIP 107 | | TIP107 |
| D407 | Schottky diode, 1A @ 40 Volts | Mot IR | 1N5817 11DQ03 |
| D408 | Gen pur Schottky diode, 1 pf or less | HP | 1N5711 |
| D401, 402, 403, 404, 601 | Si gen pur diode | | 1N4148 |
| LED602 | IR transmitter | Mot | MLED81 |
| LED601 | IR Detector | Siemens | SFH2030F |
| Q401, 402 | Power MOSFET | | IRF-510 |
| U110 | | | xx00 |
| U103, 109 | | | xx138 |
| U106, 111 | | | xx244 |
| U107, 108 | | | xx574 |
| U306 | 7574 8 bit ADC | | 7574 |
| U304 | Quad Op Amp | | LM324 |
| U202 | Quad Op Amp | | LF444 |
| U305 | 8PST CMOS Switch | MAXIM | DG508 |
| U201 | H64180 Microprocessor 6 Mhz | Hitachi Zilog | H64180 Z180 |
| U101 | Power Supervisor | MAXIM | MAX690 |
| U201 | 12 bit serial DAC | MAXIM | MAX543 |
| U203 | precision reference | MAXIM | REF02 |
| U105 | EPROM (200 ns) | | 27C512 |
| U104 | RAM 8K | | HM6264 |
| U301 | 4 Non-volatile RAM | CATALYST | 35C104 |
| VR202 | +12 Volt regulator (TO-220) | | 7812T |
| VR203 | −12 Volt regulator (TO-220) | | 7912T |
| VR201, 204 | IC LM2575T-5.0 Voltage Regulator (LM1575T-5.0 also OK) | NAT | LM2575T-5.0 |
| U401 | | | xx74 |

TABLE 1-continued

| No. | Description | Manufacturer | Part Number |
|---|---|---|---|
| U402 | MOSFET Driver | Natl | DS0026 |
| | | Teledyne | 4423 |
| | | Harris | 7667 |
| U501 | Frequency Synthesizer | Signetics | SAA1057 |
| U502 | Phase Locked Loop | Mot | 'HC4046 |
| U601 | JFET Op Amp | | LF442 |
| VR501 | 7805 Regulator (TO-220 case) | | 7805 |
| X101 | Crystal, HC-18/U holder, 12 MHZ | MTRON FOX | MP-1-12.000 |
| L201 | Inductor 100 µH 1 Amp | Caddell-Burns | CB7070-25 |
| L202 | Inductor 150 µH 5 Amp | Miller | JWM5506 |
| | | ACC | FC5-151 |
| | | DALE | IH-3-150 |
| U102 | 68 pin PLCC socket | | |
| U207 | Molex carrier socket | Molex | 78805-518 |
| BL201, 202 | Header 2 pin | | |
| CHIM | Header 2 Pin (Molex Latch Type) | | |
| BL202 | Back Light Inverter | ERG | JLA 05-2-3P |
| SEN | Header 4 Pin latching | Molex | 22-29-2041 |
| RFI, LCS, LCD | Header 20 Pin Dual Inline | | |
| KB | Header 12 Pin Single Row | | |
| SER, CAL | 4 pin bergstik | | |
| VR202 | Termalloy Heat Sink w/mtng stud | Termalloy | 6298-2-SF2-P2 |
| DISPLAY | Display Ribbon Cable 20 Pin Double Row | | |
| RFI | 20 Pin dual row header | | |
| FB401, 501, 502 | 1 bead: 501, 2; 2 Beads: 401 | JW Miller | |
| RLY401 | Omron relay | Omron | G5V-2H-12VDC |
| X401 | coupling transformer | Valor | TT1501 |
| OUT | mini-din Jack (NO sub) | Switchcraft | SMD8FRA121 |
| | | Singatron | MDJ-106-8PSC-G30 |
| SENS | 4 pin plug (key: 89-00-0422) | Molex | 10-11-2043 |
| X501 | 4 Mhz Crystal, HC-18/U Holder | M-Tron Fox | MP-1-4.000 |
| RFPC | 6 circuit mini-fit Jr. (Also -4069) | Molex | 39-29-5063 |
| Q401, 204 | Heat Sink | Termalloy | 6298-2-SF2-P2 |
| VR501 | Heat Sink | Thermally | 6038B-TT |
| FAN | 1.5" 12 VDC Fan, 7 CFM | Delta | DFB0412M |
| FAN | 2 pin locking header | Molex | |
| FAN | Matching header w/terms | Molex | |

The output transformer shown in FIG. 4 (OXFMR) has a Magnetics #A-42616-UG core, a Magnetics #PC-B2616-11 (single section) bobbin, and a Magnetics C2616-14 (with #4-40 mounting tabs) clip. The primary winding has 12 turns CT, and the secondary winding, 6 turns CT. Windings are 1 single layer, using Litz wire, and primary and secondary wires are twisted together prior to winding with 2-5 twists per inch. Two and one-half turns of the primary are wound before starting the secondary to that the secondary is physically in the center of the bobbin.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A multi-frequency ultrasound therapy device, comprising:
    a generator/control unit, comprising:
        means for generating a wave-form at multiple frequencies;
        means for controlling and monitoring a generation and output of said wave-form at any one selected frequency of said multiple frequencies, said controlling and monitoring means operably interfacing with said generating means; and
        means for amplifying the generated wave-form;
    an applicator sound head operably coupled to the generator/control unit;
    means associated with said amplifying means for supplying the amplified wave-form to the applicator sound head as electrical signals; and
    means associated with the applicator sound head for converting said electrical signals into multi-frequency ultrasound waves, said converting means in association with said applicator sound head for operating at a first desired resonant frequency, a second desired resonant frequency and a third desired resonant frequency.

2. A multi-frequency ultrasound therapy device as defined in claim 1 wherein the means for controlling and monitoring the generation and output of said wave-form comprises a microprocessor.

3. A multi-frequency ultrasound therapy device as defined in claim 1 wherein the means for generating said wave-form at multiple frequencies comprises a precision oscillator.

4. A multi-frequency ultrasound therapy device as defined in claim 3, further comprising wave shaping circuitry and wherein the precision oscillator provides an output to said wave shaping circuitry.

5. A multi-frequency ultrasound therapy device as defined in claim 1 wherein the means for amplifying the generated wave-form comprises at least one output amplifier.

6. A multi-frequency ultrasound therapy device as defined in claim 1 further comprising a thermistor which monitors an operating temperature of the applicator sound head and disables the means for generating a wave-form at multiple frequencies when the operating temperature of the applicator sound head exceeds a pre-set safety level.

7. A multi-frequency ultrasound therapy device as defined in claim 1 further comprising at least two electrodes having an electrical lead connection from the generator/control unit, said electrodes operably connected to said converting means.

8. A multi-frequency ultrasound therapy device as defined in claim 1 wherein said converting means comprises a crystal transducer formed of a ceramic material and bonded to an applicator member disposed with the applicator sound head.

9. A multi-frequency ultrasound therapy device as defined in claim 8 wherein said crystal transducer further comprises a natural resonance frequency at approximately 2 Mhz.

10. A multi-frequency ultrasound therapy device as defined in claim 8 wherein the ceramic crystal transducer is formed so as to be one-half wavelength thick at approximately 2 MHz.

11. A multi-frequency ultrasound therapy device as defined in claim 8 wherein the applicator member is formed of an aluminum alloy.

12. A multi-frequency ultrasound therapy device as defined in claim 8 wherein the applicator member is formed so as to have a natural resonance frequency at approximately 2 MHz.

13. A multi-frequency ultrasound therapy device as defined in claim 1 wherein the applicator sound head provides said first desired resonant frequency at approximately 2 MHz, said second desired resonant frequency at approximately 1 MHz and said third desired resonant frequency at approximately 3 MHz.

14. A multi-frequency ultrasound therapy device as defined in claim 1 wherein said converting means comprises a crystal transducer and an aluminum alloy applicator member being fabricated to thickness and flatness tolerances of 0.0005 inch (0.01270 mm).

15. A multi-frequency ultrasound therapy device as defined in claim 14 wherein the crystal transducer and the aluminum alloy applicator member further comprises a fixation bond formed therebetween having a near zero thickness.

16. A multi-frequency ultrasound therapy device as defined in claim 1 wherein said applicator sound head produces said first, second, and third resonant frequencies at approximately 1 MHz, 2 MHz and 3 MHz, respectively to facilitate three different depths of tissue penetration.

17. A multi-frequency ultrasound therapy device comprising:

a generator/control unit, comprising:
  a precision oscillator having wave shaping circuitry for generating a wave-form at multiple frequencies;
  a microprocessor for controlling and monitoring a generation and output of said wave-form at any one selected frequency of said multiple frequencies, said microprocessor operably interfacing with said precision oscillator; and
  at least one output amplifier for amplifying the generated wave-form;

an applicator sound head operably coupled to said generator/control unit;

means associated with said output amplifier for supplying the amplified wave-form to the applicator sound head as electrical signals;

a thermistor interfaced with the microprocessor for monitoring an operating temperature of the applicator sound head and disabling the precision oscillator when the operating temperature of the applicator sound head exceeds a safety level;

at least two electrodes having an electrical connection leading from the generator/control unit;

an aluminum alloy applicator member;

a crystal transducer formed of a ceramic and bonded to said applicator member, the crystal transducer being operably coupled to said electrodes for converting said electrical signals into multi-frequency ultrasound waves, the crystal transducer and the applicator member in association with the applicator sound head for operating at a first desired resonant frequency, a second desired resonant frequency and a third desired resonant frequency.

18. A multi-frequency ultrasound therapy device as defined in claim 17 wherein the crystal transducer and the applicator member, in combination, provides said first desired resonant frequency at approximately 2 MHz, said second desired resonant frequency at approximately 1 MHz and said third desired resonant frequency at approximately 3 MHz to facilitate at least three different depths of tissue penetration.

19. A multi-frequency ultrasound therapy device as defined in claim 17 wherein the crystal transducer and the applicator member are fabricated to thickness and flatness tolerances of 0.0005 inch (0.01270 mm).

20. A method for calibrating a multi-frequency sound head, the method comprising the steps of:

obtaining an applicator sound head having a transducer providing a natural resonance at a first desired frequency, with additional resonances at a second desired frequency and a third desired frequency;

scanning the applicator sound head at a first temperature through at least three output frequencies;

determining a specific driving frequency of maximum efficiency at each of said output frequencies;

calculating an impedance of the applicator sound head from detected output voltage and current at each of said output frequencies;

scanning the applicator sound head at a second temperature being higher than the first temperature;

detecting a change in said driving frequency of maximum efficiency at each of said scanned output frequencies;

storing for each of said three output frequencies the head impedance and the driving frequency change;

generating a multi-frequency wave-form;

amplifying said multi-frequency wave-form;

delivering the amplified multi-frequency wave-form to the applicator sound head as high-frequency electrical signals;

converting the high-frequency electrical signals into ultrasonic waves;

monitoring the temperature and output current of the applicator sound head; and calibrating the driving frequency to maintain a level of optimum ultrasonic output.

* * * * *